United States Patent
Sullivan et al.

(10) Patent No.: US 9,631,998 B2
(45) Date of Patent: Apr. 25, 2017

(54) APPARATUS AND METHOD FOR ASSISTING WITH FLUID PRESSURE MEASUREMENT

(71) Applicants: Anne M. Sullivan, Redondo Beach, CA (US); Russell V. Westhphal, Atascadero, CA (US); Brittany Reanne Kinkade, Redondo Beach, CA (US); James Alan Gerhardt, Atascadero, CA (US)

(72) Inventors: Anne M. Sullivan, Redondo Beach, CA (US); Russell V. Westhphal, Atascadero, CA (US); Brittany Reanne Kinkade, Redondo Beach, CA (US); James Alan Gerhardt, Atascadero, CA (US)

(73) Assignee: Northrop Grumman Systems Corporation, Falls Church, VA (US)

( * ) Notice: Subject to any disclaimer, the term of this patent is extended or adjusted under 35 U.S.C. 154(b) by 132 days.

(21) Appl. No.: 14/701,014

(22) Filed: Apr. 30, 2015

(65) Prior Publication Data

US 2015/0346078 A1    Dec. 3, 2015

Related U.S. Application Data (60) Provisional application No. 62/004,576, filed on May 29, 2014.

(51) Int. Cl.
| | |
|---|---|
| G01L 7/00 | (2006.01) |
| G01L 19/14 | (2006.01) |
| G01L 7/02 | (2006.01) |
| G01L 19/00 | (2006.01) |
| G01N 19/02 | (2006.01) |
| G01M 9/06 | (2006.01) |

(52) U.S. Cl.
CPC .............. *G01L 19/147* (2013.01); *G01L 7/00* (2013.01); *G01L 7/024* (2013.01);
(Continued)

(58) Field of Classification Search
CPC . G01L 7/00; G01L 7/022; G01L 7/024; G01L 7/182; G01L 7/185; G01L 19/00;
(Continued)

(56) References Cited

U.S. PATENT DOCUMENTS

| | | | | |
|---|---|---|---|---|
| 4,072,049 A | * | 2/1978 | Miller | G01M 9/06 73/147 |
| 4,240,290 A | | 12/1980 | Montoya et al. | |
| 4,414,851 A | * | 11/1983 | Maglic | G01L 19/14 361/283.3 |

OTHER PUBLICATIONS

International Search Report for corresponding PCT/US2015/028575 dated Aug. 24, 2015; Completed by Jean-Luc Kaiser on Aug. 14, 2015.

(Continued)

*Primary Examiner* — Benjamin Schmitt
(74) *Attorney, Agent, or Firm* — Tarolli, Sundheim, Covell & Tummino LLP (57) ABSTRACT

An apparatus for assisting with measurement of a fluid pressure includes a cover layer having a leading cover edge and upper and lower cover surfaces. A cover aperture fluidly connects the upper and lower cover surfaces. A spacer layer has oppositely facing upper and lower spacer surfaces. A cavity has an upper cavity surface, defined by the lower cover surface, which includes the leading cover edge and the cover aperture. A measuring tube is located adjacent to the upper cover surface. The measuring tube includes a tube lumen. When the lower spacer surface is connected to the substrate, the substrate defines a lower cavity surface and extant fluid is present within the cavity. Variable fluid flowing toward the cavity exerts pressure on the extant fluid to generate an extant fluid pressure level which is physically transmitted through the apparatus and made available for measurement as an extant fluid pressure level.

20 Claims, 9 Drawing Sheets

(52) U.S. Cl.
CPC ........ *G01L 19/0038* (2013.01); *G01L 19/149* (2013.01); *G01M 9/065* (2013.01); *G01N 19/02* (2013.01)

(58) Field of Classification Search
CPC . G01L 19/0007; G01L 19/0038; G01L 19/14; G01L 19/147; G01L 19/149; G01M 9/00; G01M 9/06; G01M 9/062; G01M 9/065
USPC .......................................... 73/147, 700, 756
See application file for complete search history.

(56) References Cited

OTHER PUBLICATIONS

Edwards, "Measurement of Skin-Friction Using Surface-Pitot Tubes in Free Flight at Supersonic Speeds", Aeronautical *Reseach Council*, C.P. No. 711 (1964).
Hopkins, et al., "Study of Surface Pitots for Measuring Turbulent Skin Friction at Supersonic Mach Numbers—Adiabatic Wall", *NASA TN D-3478* (1966).
EAST: "*Measurement of skin friction at low subsonic speeds by the razor-blade technique*" HM Stationery Office, 1966.
Gadd: "*A Note on the Theory of the Stanton Tube*"; HM Stationery Office, 1960.
Rechenberg, I. "*Measurement of turbulent skin-friction with the preston tube.*" (1962).
Stanton, et al.: "*On the conditions at the boundary of a fluid in turbulent motion*"; Proceedings of the Royal Society of London. Series A, Containing Papers of a Mathematical and Physical Character (1920): 413-434.

* cited by examiner

FIG. 10

APPARATUS AND METHOD FOR ASSISTING WITH FLUID PRESSURE MEASUREMENT

RELATED APPLICATION

This application claims priority from U.S. Provisional Application No. 62/004,576, filed 29 May 2014, the subject matter of which is incorporated herein by reference in its entirety.

TECHNICAL FIELD

This disclosure relates to an apparatus and method for assisting with a fluid pressure measurement and, more particularly, to a method and apparatus for creating a locally disturbed fluid pressure at/near a surface of a substrate and assisting with measuring that fluid pressure, such as through locally disturbing a boundary layer fluid pressure to assist with skin friction observations.

BACKGROUND

In physics and fluid mechanics, a boundary layer is the layer of fluid in the immediate vicinity of a surface of interest, where the effects of viscosity may be significant. On an aircraft wing, for example, the boundary layer is the part of the flow closest to the surface of the wing, where viscous forces distort the surrounding non-viscous flow.

In high-performance aerospace and aeronautics designs, such as those for gliders and commercial aircraft, significant resources are devoted to controlling the behaviour of the boundary layer to minimize drag. Two effects should to be considered in this effort. First, the shear forces at the surface of the wing create skin friction drag. Second, the boundary layer adds to the effective thickness of the body, via the displacement thickness, thereby increasing the pressure drag. Third, the boundary layer can separate in a region of local deceleration, creating drastic, often detrimental changes in aerodynamic performance. In order to control, or even understand, boundary layer behaviour, it is therefore desirable to measure and/or calculate fluid pressures, skin friction, and other properties of airflow past a surface of interest.

Stanton gauges are commonly used to measure local skin friction coefficients (and thereby also at least help to determine boundary layer state). The advantage that a Stanton gauge has over other similar, known methods, such as Preston tubes, is that the Stanton gauge calibration is much less dependent upon boundary layer state, making the analysis of the data much simpler. However, Stanton gauges require existing surface static pressure taps to obtain the pressure at the Stanton gauge, which is a modified or disturbed pressure. A local static reference pressure—and, preferably, temperature—are also used to calculate the skin friction in a known manner. Though most wind tunnel models have integral static pressure taps, flight test assets—whether a model or an operational aircraft—rarely do.

SUMMARY

In an embodiment, an apparatus for assisting with measurement of the pressure of a variable fluid is described. The variable fluid is flowing past a substantially planar, constant-surface substrate in a substantially linear and longitudinal local fluid flow direction. The apparatus comprises a substantially planar cover layer having longitudinally spaced leading and trailing cover edges, laterally spaced first and second cover side edges, and oppositely facing upper and lower cover surfaces transversely separated by a cover layer thickness. At least the lower cover surface defines a cover layer footprint in a longitudinal-lateral plane. A cover aperture extends through the cover layer thickness to fluidly connect the upper and lower cover surfaces. A substantially planar spacer layer has longitudinally spaced leading and trailing spacer edges, laterally spaced first and second spacer side edges, and oppositely facing upper and lower spacer surfaces transversely separated by a spacer layer thickness. At least the lower spacer surface defines a spacer layer footprint in the longitudinal-lateral plane. The spacer layer footprint has a smaller area than the area of the cover layer footprint. The spacer layer footprint is bounded in the longitudinal-lateral plane by a spacer layer perimeter. A cavity has an upper cavity surface defined by the lower cover surface. The upper cavity surface includes the leading cover edge and the cover aperture. The cavity has a side cavity perimeter in the longitudinal-lateral plane at least partially defined by the spacer layer perimeter. A measuring tube has leading and trailing tube ends longitudinally separated by a tube body. The measuring tube is located adjacent to the upper cover surface. The leading tube end has a length which is a superminority of the length of the tube body. The measuring tube includes a tube lumen extending longitudinally through the tube body between a leading lumen aperture at the leading tube end and a trailing lumen aperture longitudinally spaced from the leading lumen aperture. The leading lumen aperture is in fluid communication with the cavity via the cover aperture. The trailing lumen aperture is in fluid communication with a pressure measuring device. When the lower spacer surface is connected to the substrate, the substrate defines a lower cavity surface. Extant fluid is at least partially contained within the cavity, and variable fluid flowing in the local fluid flow direction interacts with the extant fluid within the cavity at least adjacent the leading cover edge. At least a portion of the variable fluid flowing in the local fluid flow direction exerts pressure upon the extant fluid to generate an extant fluid pressure level which is physically transmitted from the cavity through the cover aperture, into the tube lumen through the leading lumen aperture, and is made available for measurement, as an extant fluid pressure value, through at least a portion of the tube lumen.

In an embodiment, an apparatus for assisting with measurement of the boundary layer pressure of a variable fluid is described. The variable fluid is flowing through an ambient space past a substantially planar, constant-surface substrate in a substantially linear and longitudinal local fluid flow direction. The apparatus comprises a substantially planar cover layer having longitudinally spaced leading and trailing cover edges, laterally spaced first and second cover side edges, and oppositely facing upper and lower cover surfaces transversely separated by a cover layer thickness. A cover aperture extends through the cover layer thickness to fluidly connect the upper and lower cover surfaces. A substantially planar spacer layer has longitudinally spaced leading and trailing spacer edges, laterally spaced first and second spacer side edges, and oppositely facing upper and lower spacer surfaces transversely separated by a spacer body having a spacer layer thickness. The spacer layer defines a spacer layer perimeter in a longitudinal-lateral plane. The spacer layer perimeter defines a concave extension into the spacer body which bifurcates the leading spacer edge but is longitudinally spaced from the trailing spacer edge. A cavity has an upper cavity surface defined by the lower cover surface. The upper cavity surface includes a cover aperture. The cavity has a side cavity perimeter in the longitudinal-lateral plane at least partially defined by concave extension of the spacer layer perimeter. The cavity is in fluid communication with the ambient space at the leading spacer edge. A measuring tube has leading and trailing tube ends longitudinally separated by a tube body. The measuring tube is located adjacent to the upper cover surface. The leading tube end has a length which is a superminority of the length of the tube body. The measuring tube includes a tube lumen extending longitudinally through the tube body between a leading lumen aperture at the leading tube end and a trailing lumen aperture longitudinally spaced from the leading lumen aperture. The leading lumen aperture is in fluid communication with the cavity via the cover aperture. The trailing lumen aperture is in fluid communication with a pressure measuring device. When the lower spacer surface is connected to the substrate, the substrate defines a lower cavity surface. Extant fluid is at least partially contained within the cavity, and variable fluid flowing in the local fluid flow direction interacts with the extant fluid within the cavity at least adjacent the leading cover edge. At least a portion of the variable fluid flowing in the local fluid flow direction exerts pressure upon the extant fluid to generate an extant fluid pressure level which is physically transmitted from the cavity through the cover aperture, into the tube lumen through the leading lumen aperture, and is made available for measurement, as an extant fluid pressure value, through at least a portion of the tube lumen.

In an embodiment, a method of assisting with measurement of the pressure of a variable fluid is described. The variable fluid is flowing through an ambient space past a substantially planar, constant-surface substrate in a substantially linear and longitudinal local fluid flow direction. A pressure observation device is adhered to the substrate. The pressure observation device includes a cover layer transversely spaced from the substrate by the spacer layer. The cover layer, spacer layer, and substrate collectively form a cavity having a lateral cavity width and a longitudinal cavity depth that are both significantly larger than a transverse cavity height. The cavity is open to the ambient space at a leading edge of the pressure observation device. The cavity is substantially closed, other than through a cover aperture extending through the cover layer, adjacent a trailing surface of the cavity longitudinally spaced, in the local fluid flow direction, from the leading edge of the pressure observation device. Extant fluid is at least partially contained within the cavity. Variable fluid flow in the local fluid flow direction is directed toward the cavity pressure observation device to interact with the extant fluid within the cavity at least adjacent the leading edge of the pressure observation device. An extant fluid pressure level is generated through pressure of the variable fluid flow upon the extant fluid within the cavity. The extant fluid pressure level is physically transmitted from the trailing surface of the cavity through the cover layer via the cover aperture. The pressure observation device is provided with a measuring tube including a tube lumen extending longitudinally through a tube body between a leading lumen aperture at the leading tube end and a trailing lumen aperture longitudinally spaced from the leading lumen aperture. The extant fluid pressure level is physically transmitted through the cover aperture of the cover layer into the leading lumen aperture. The extant fluid pressure level is physically transmitted through at least a portion of the tube lumen toward the trailing lumen aperture. An extant fluid pressure value is generated in response to the extant fluid pressure level at the trailing lumen aperture.

BRIEF DESCRIPTION OF THE DRAWINGS

For a better understanding, reference may be made to the accompanying schematic drawings, in which.

DESCRIPTION OF ASPECTS OF THE DISCLOSURE

This technology comprises, consists of, or consists essentially of the following features, in any combination.

Figure 1:
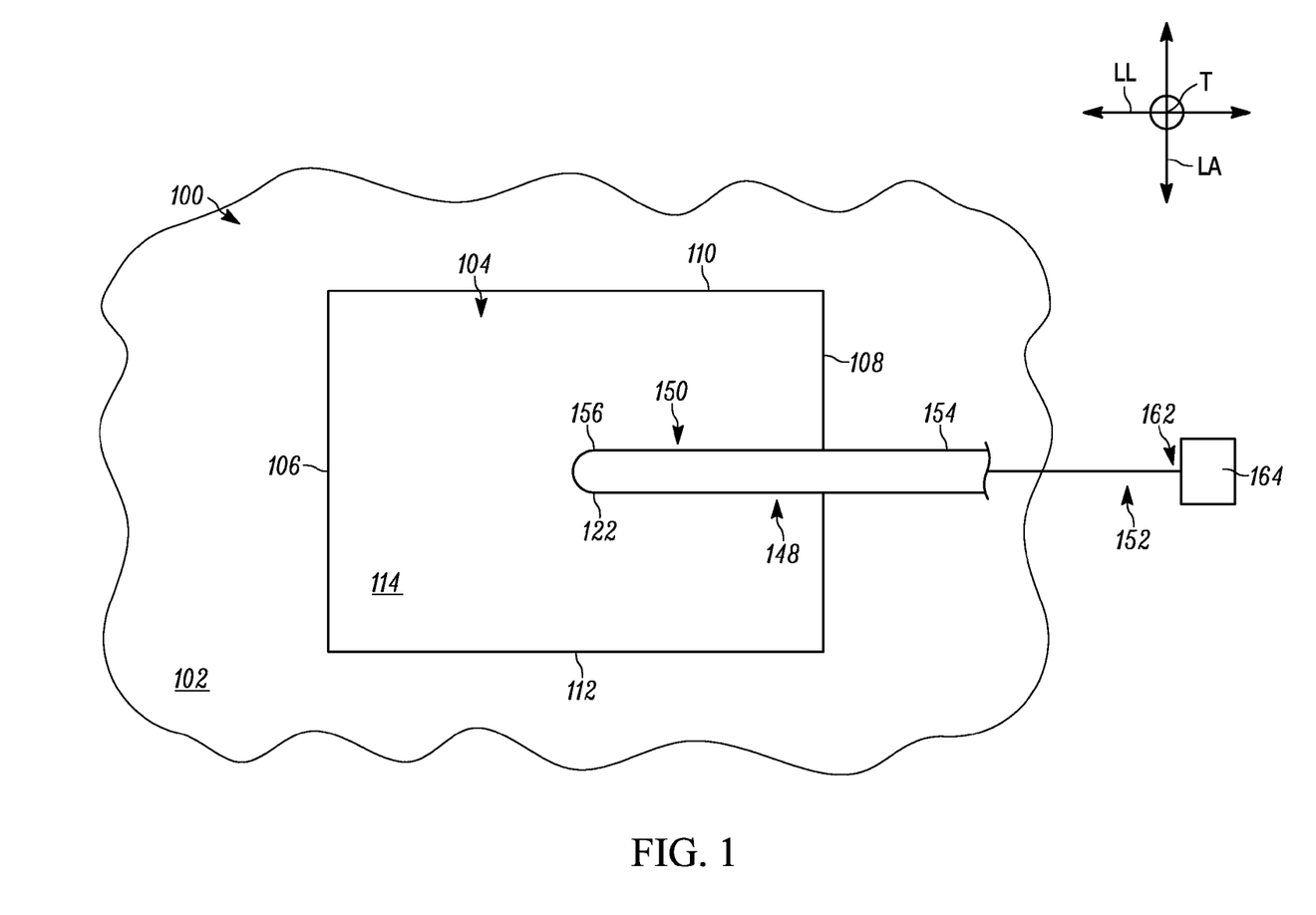
FIG. 1 is a schematic top view of one embodiment.
Figure 2:
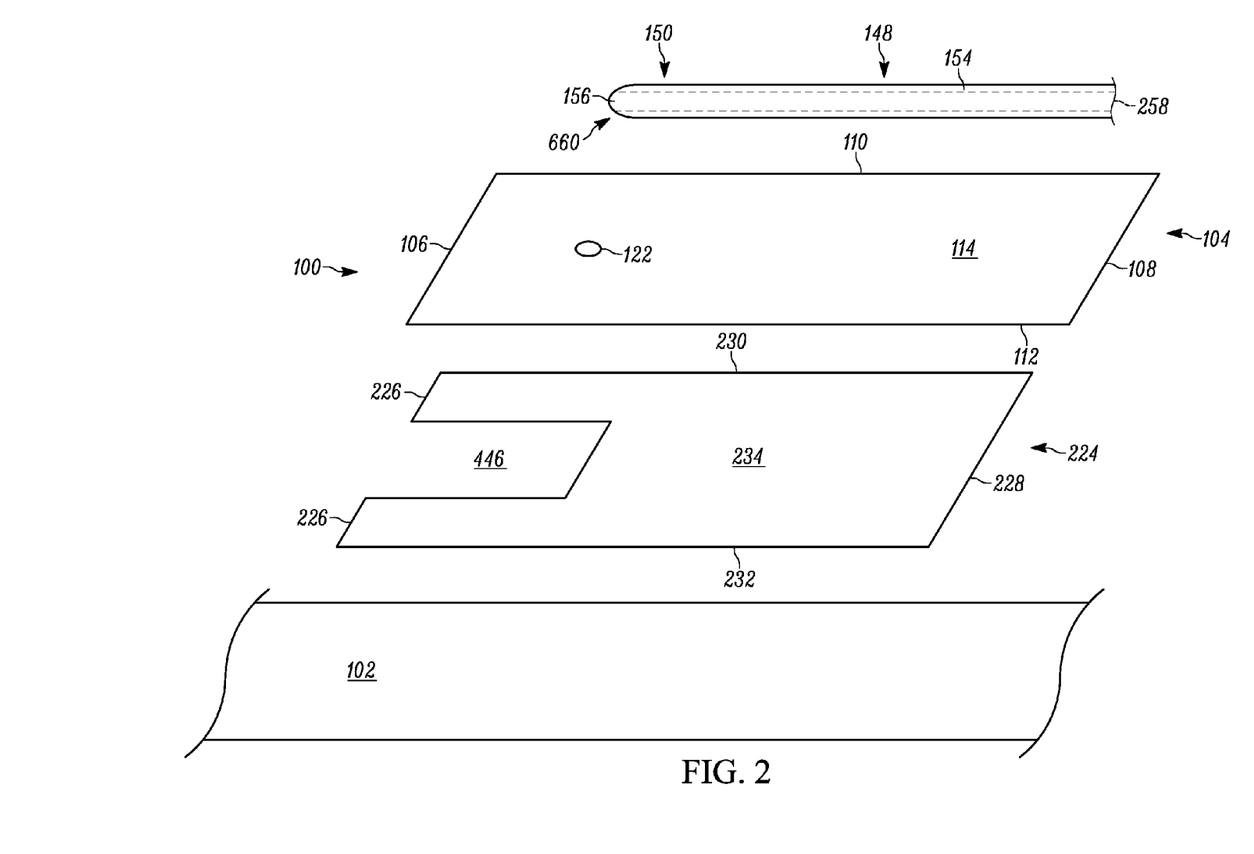
FIG. 2 is an exploded side perspective view of the embodiment of FIG. 1.
Figure 3:
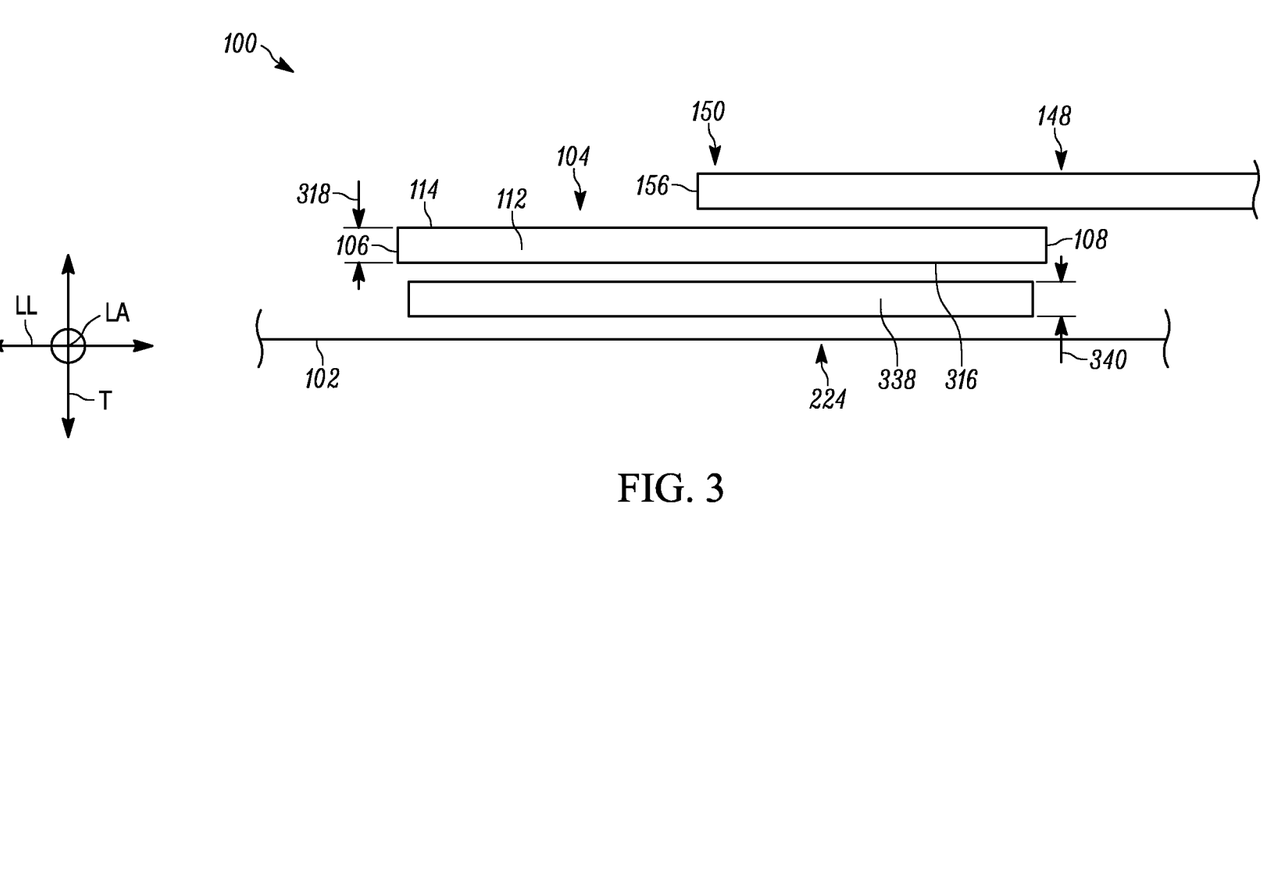
FIG. 3 is a schematic side view of the embodiment of FIG. 1.

FIG. 1 depicts an apparatus 100, shown here as a pressure observation device, for creating a locally disturbed fluid pressure at/near a surface of a substrate and assisting with measuring that fluid pressure. For example, a fluid pressure measurement could be facilitated by the apparatus 100 such as through locally disturbing a boundary layer fluid pressure to assist with skin friction observations—i.e., by creating a disturbed pressure and assisting with measurement of that disturbed pressure within a variable fluid flow region. The description herein references a variable fluid flowing through an ambient space past a substantially planar, constant-surface substrate 102 in a substantially linear and longitudinally oriented local variable fluid flow direction. A "variable" fluid, as referenced herein, is a fluid for which a fluid pressure measurement is desired—often, the fluid pressure measurement is desired because the fluid pressure changes ("varies") over time. The term "variable" is used herein to indicate that the fluid pressure is not constant, and no specific implication or indication is made or intended herein, by the use of "variable" to describe the fluid, as to the content/makeup/components of the fluid possibly being heterogeneous, homogeneous, or having any other properties. The "substrate" 102 is primarily used herein to indicate a portion of a surface of interest underneath the apparatus 100, but one of ordinary skill in the art will understand that, depending upon context, a "substrate" could also or instead encompass some area of the surface of interest in close proximity to, but not necessarily directly beneath, the apparatus 100.

While the description herein uses air flowing past an aircraft surface as an example of a variable fluid, any fluid, including but not limited to, any homogenous or heterogeneous gas, liquid, smoke or particle-carrying fluid, or other fluid could be considered to be a variable fluid and thus have a pressure measurement facilitated by the apparatus 100. Similarly, any suitable surface of interest, for which a boundary layer fluid pressure is desired to be measured, could serve as the substrate 102. The term "constant-surface" is used herein to indicate a substrate 102 that is substantially unbroken across a region of area of interest, such as by being substantially devoid of apertures, discontinuities, protrusions, and, for the described example, static pressure taps. It is contemplated that a "constant-surface" substrate could include some minor inclusions, particularly if accidental or wear-caused (i.e., not originally intended to be present), but the accuracy of the fluid pressure measurement by the apparatus 100 may be affected if the substrate 102 has significant deviations from a constant-surface state. The ambient space simply refers to the volume surrounding the substrate 102, such as the air located outside an aircraft when the substrate is a wing surface of that aircraft. It is contemplated that variable fluid flow across an entirety of the substrate 102 could be nonuniform in direction and/or orientation, but will be presumed to be locally substantially longitudinally oriented, for the purposes of this description.

The longitudinal direction is shown and described herein as being substantially parallel to the longitudinal axis LL (the left-right direction, in the orientation of FIG. 1), with the lateral direction being substantially perpendicular to longitudinal (i.e., along lateral axis LA, the up-down direction, in the orientation of FIG. 1), and the transverse direction being substantially perpendicular to both longitudinal and lateral (i.e., along transverse axis T, into and out of the page, in the orientation of FIG. 1).

As shown in FIGS. 1-5, the apparatus 100 includes a substantially planar cover layer 104 having longitudinally spaced leading and trailing cover edges 106 and 108, respectively; laterally spaced first and second cover side edges 110 and 112, respectively; and oppositely facing upper and lower cover surfaces 114 and 316, respectively, transversely separated by a cover layer thickness 318. The cover layer 104 may be substantially rigid, for some use environments, and may be made from any desired material such as, but not limited to, stainless steel or any other metal, glass, plastic, or any other suitable material or combination thereof. For example, the cover layer 104 may be at least partially made from stainless steel shim stock having a thickness in the range of, for example, 0.002 inches (0.0508 millimeters) to 0.005 inches (0.127 millimeters) and, more specifically, about 0.003 inches (0.0762 millimeters). The terms "leading" and "trailing" are used herein to refer to directions upstream and downstream, respectively, as compared to a direction of local, substantially longitudinal variable fluid flow.

Figure 4:
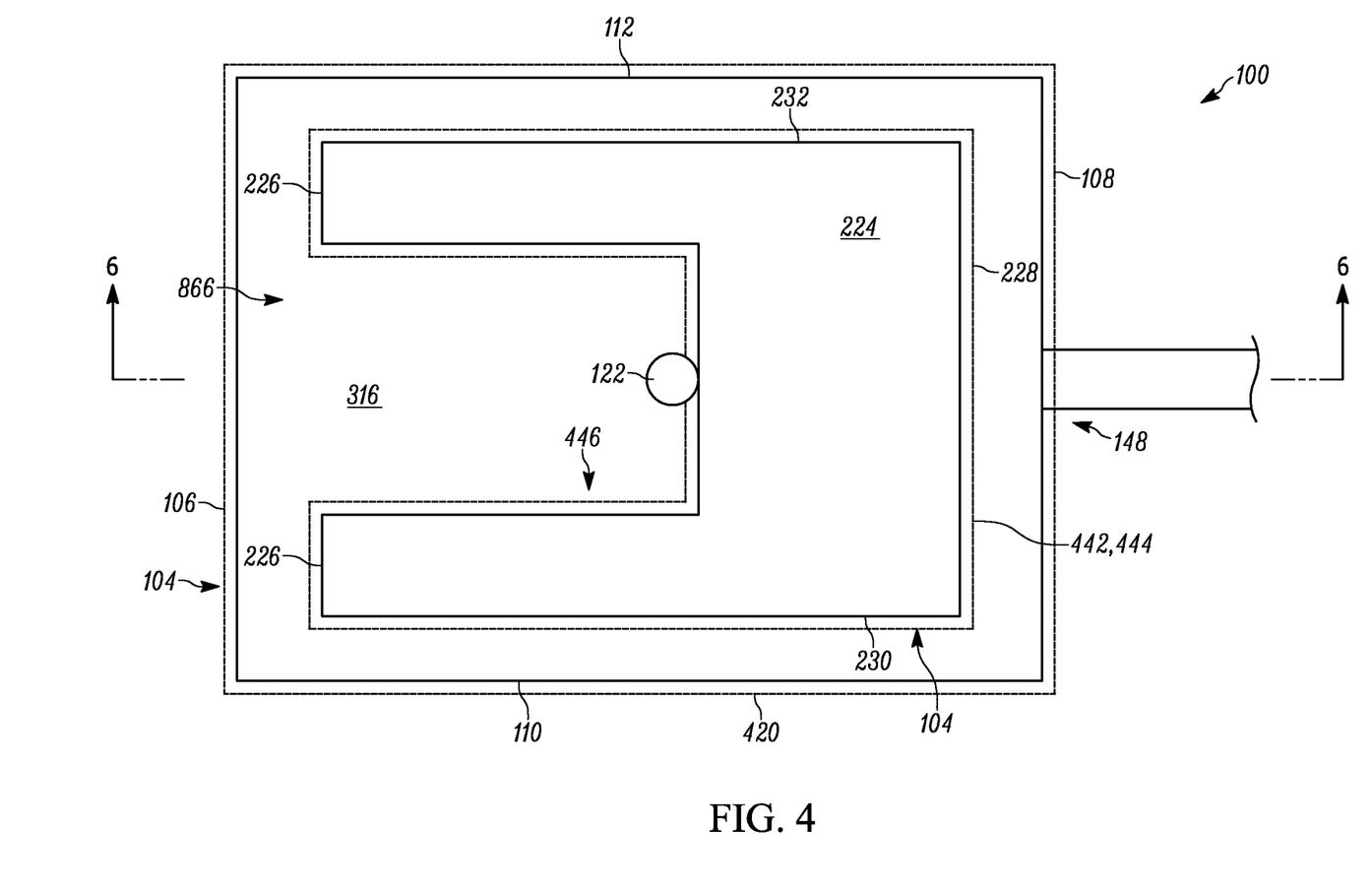
FIG. 4 is a schematic bottom view of the embodiment of FIG. 1.
Figure 5:
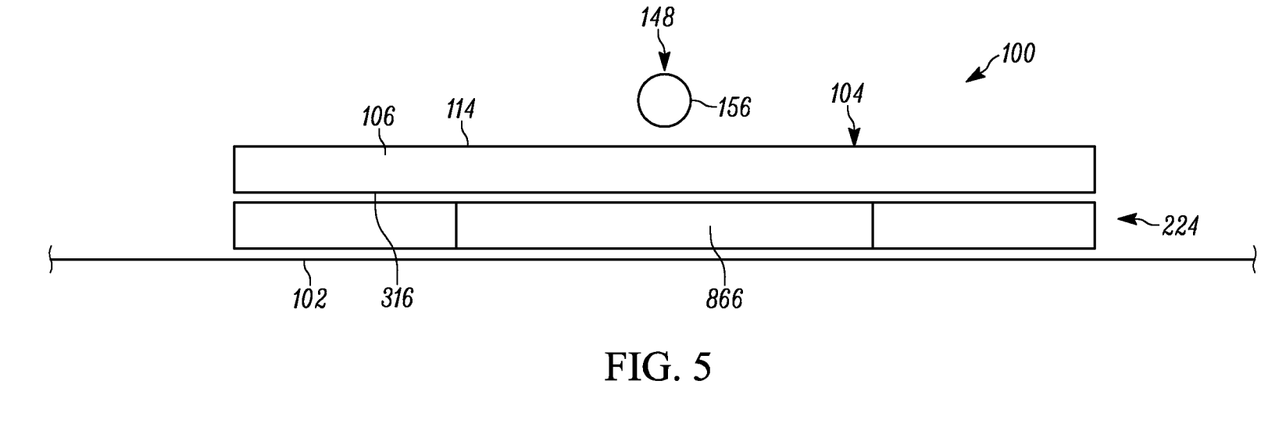
FIG. 5 is a schematic front view of the embodiment of FIG. 1.

At least the lower cover surface 316 defines a cover layer footprint 420 in a longitudinal-lateral plane. As shown in FIG. 4, this cover layer footprint 420 is substantially quadrilateral, and more specifically a rectangle, but the cover layer footprint 420 could have any desired configuration for a particular use environment. For example, one or more of the leading and trailing cover edges 106 and 108 and/or first and second cover side edges 110 and 112 could be angled, nonlinear, curved, curvilinear, partially linear, or have any other desired configuration, as provided by one of ordinary skill in the art.

Figure 6:
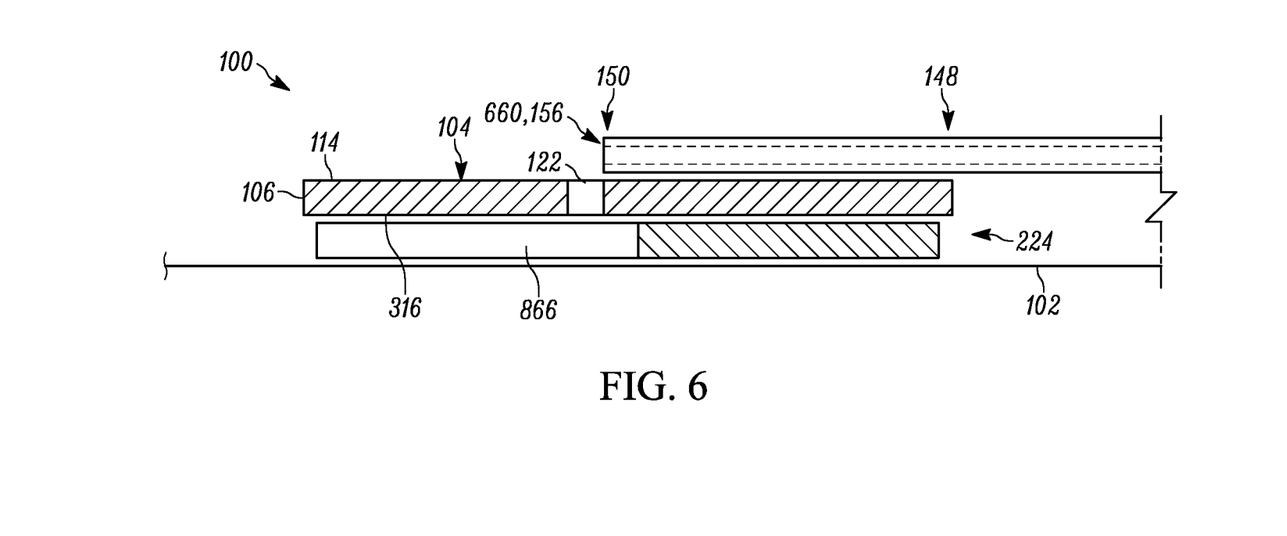
FIG. 6 is a cross-sectional view taken along line 6-6 of FIG. 4.

A cover aperture 122 extends through the cover layer thickness 420 to fluidly connect the upper and lower cover surfaces 114 and 316. The cover aperture 122 can be configured for a particular use environment by one of ordinary skill in the art to have any suitable shape, size, placement on the cover layer 104, orientation with respect to the cover layer thickness 420, or other physical properties, but is shown in the Figures (see, e.g., FIG. 6) and described herein as being a relatively small, round hole extending substantially perpendicularly through the cover layer thickness 420.

The apparatus 100 also includes a substantially planar spacer layer 224 having longitudinally spaced leading and trailing spacer edges 226 and 228, respectively; laterally spaced first and second spacer side edges 230 and 232, respectively; and oppositely facing upper and lower spacer surfaces 234 and 436, respectively. The upper and lower spacer surfaces 234 and 436 are transversely separated by a spacer body 338 having a spacer layer thickness 340. The spacer layer 224 may be made from any suitable material, having any desirable flexibility and compression characteristics. Example materials for the spacer layer 224 include, but are not limited to, foams, papers, tapes, adhesives, epoxies, or any other desired materials or combinations of materials. Optionally, at least a portion of the lower spacer surface 436 includes an adhesive (not shown) configured to selectively adhere the apparatus 100 to the substrate 102 and/or substantially prevent undesired fluid flow between components of the apparatus 100. As an example, one suitable material for the spacer layer 224 is F9460PC VHB adhesive transfer tape, available from 3M of St. Paul, Minn., and having a thickness of 0.002 inch (0.0508 millimeter).

At least the lower spacer surface 436 defines a spacer layer footprint 442 in the longitudinal-lateral plane. The spacer layer footprint 442 may have a smaller area than the area of the cover layer footprint 420, such as the "U" shaped spacer layer footprint 442 shown in the Figures. The spacer layer footprint 442 is bounded in the longitudinal-lateral plane by a spacer layer perimeter 444. The spacer layer footprint 442 may define, as shown in FIG. 4, a concave extension 446 extending into the spacer body 338 in at least the longitudinal-lateral plane, the concave extension 446 bifurcating the leading spacer edge 226 but being longitudinally spaced from the trailing spacer edge 228.

A measuring tube 148 of the apparatus 100 includes leading and trailing tube ends 150 and 152 (shown schematically), respectively, longitudinally separated by a tube body 154. The measuring tube 148 is located adjacent to the upper cover surface 114 and may be adhered to, or otherwise at least partially connected, directly or indirectly, to the upper cover surface 114. The leading tube end 150 has a length which is a superminority of the overall length of the tube body 154. The term "superminority" is used here to indicate to indicate a length which is significantly less than half of the overall length. Here, a "superminority" does not restrict the leading tube end 150 to being just the absolute extreme longitudinal end surface (the longitudinally forward tip 156) of the measuring tube 148, but the leading tube end 150 could also be considered to extend some slight or minor distance, compared to the overall tube length, longitudinally back from the longitudinally forward tip 156 to encompass at least a portion of the tube body 154.

The measuring tube 148 includes a tube lumen 258 extending longitudinally through the tube body 154 between a leading lumen aperture 660 at the leading tube end 150 (as will be discussed below) and a trailing lumen aperture (shown schematically at 162) longitudinally spaced from the leading lumen aperture 660 along the tube body 154. The trailing lumen aperture 162 can be, but is not necessarily, located at or near the trailing tube end 152. The leading lumen aperture 660 is in fluid communication with the cover aperture 122, and the trailing lumen aperture 152 is in fluid communication with a pressure measuring device, shown schematically at 164. The measuring tube 148 may be at least partially made, for example, from a hypodermic tube having any suitable dimensions, materials, or other physical characteristics. As shown in the Figures, for example, the measuring tube 148 could be made from stainless steel hypodermic tubing, having an outside diameter of 0.020 inches (0.508 millimeters), an inside diameter of 0.012 inches (0.3048 millimeters), and having any length, such as one inch (25.4 millimeters). Optionally, the measure tube 148 could also or instead comprise a relatively long, possibly flexible extension tube (not shown), to communicate a fluid pressure level to a remotely located measuring device, as discussed below. It is contemplated that, for many use environments, the extreme longitudinally forward tip 156 of the hypodermic tube measuring tube 148 could be closed ("blind"), with the leading lumen aperture 660 extending substantially radially through the tube body 154 at a location spaced back (even if very slightly) from the longitudinally forward tip 156. However, one of ordinary skill in the art could configure a measuring tube 148 as desired.

Figure 7A:
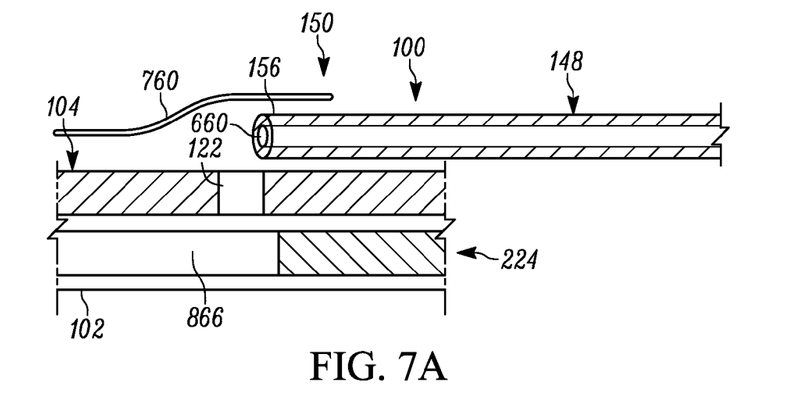
FIG. 7A is a schematic partial view of an alternate configuration of FIG. 6.
Figure 7B:
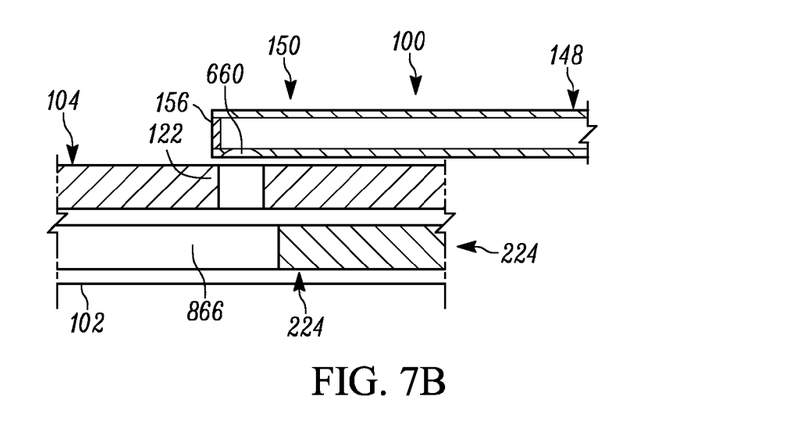
FIG. 7B is a schematic partial view of an alternate configuration of FIG. 6.
Figure 7C:
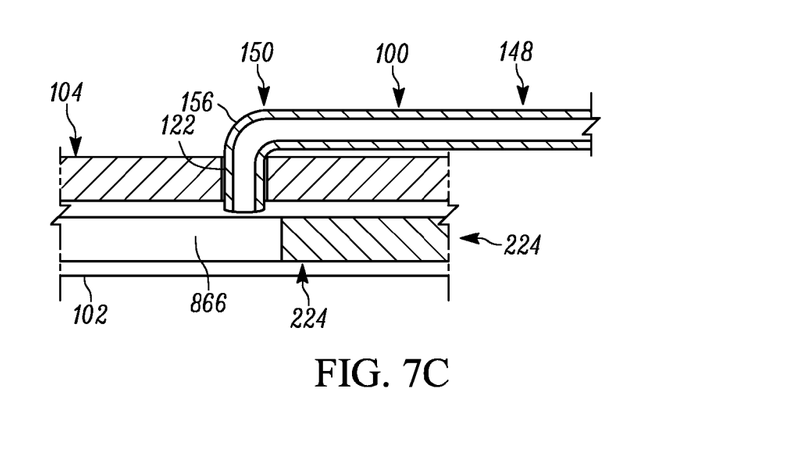
FIG. 7C is a schematic partial view of an alternate configuration of FIG. 6.

With reference to FIGS. 7A-7C, some example configurations of the measuring tube 148, including the leading tube end 150 and leading lumen aperture 660, are shown in relation to the cover aperture 122. In FIG. 7A, the leading lumen aperture 660 is located at the longitudinally forward tip 156 portion of the leading tube end 150. Optionally, to assist fluid communication in any embodiment, a thin piece of tape or another covering element 760 (shown schematically in FIG. 7A) may be placed over at least a portion of the leading tube end 150 and the cover aperture 122. The covering element 760, when present, could help block variable fluid flow from entering the leading lumen aperture 660 directly.

In FIG. 7B, the leading lumen aperture 660 is still located at a portion of the measuring tube 148 which can reasonably be considered to be the leading tube end 150, but the leading lumen aperture 660 extends through the tube body 154 at a location longitudinally spaced slightly back from the extreme longitudinally forward tip 156 portion (which is closed off to prevent ingress of ambient fluid) of the leading tube end 150. For example, when the measuring tube 148 is made at least partially from a hypodermic tube, a small bead of solder or other material, provided in any suitable way, can be used to "plug" the originally-open extreme longitudinally forward tip 156 portion, and the lumen aperture 660 can be drilled laterally through the tube body 154.

In the arrangements shown in both FIGS. 7A and 7B, the leading lumen aperture 660 is located just above the cover aperture 122, and one of ordinary skill in the art can readily configure the apparatus 100 to place the cover aperture 122 and leading lumen aperture 660 into a desired fluid-communicating relationship (e.g., by spacing the cover aperture 122 and leading lumen aperture 660 a desired distance apart and/or by aligning the cover aperture 122 and leading lumen aperture 660 in a predetermined manner, including bringing these two apertures into substantially direct, anastomosis-like contact).

In contrast, the embodiment shown in FIG. 7C includes a bend in the measuring tube 148 to place at least a portion of the leading tube end 150 into at least a portion of the cover aperture 122. In this manner, the leading lumen aperture 660 can be placed directly into fluid communication with a cavity 866 at least partially defined by the lower cover surface 316, as will now be discussed with particular reference to FIGS. 8-10.

Figure 8:
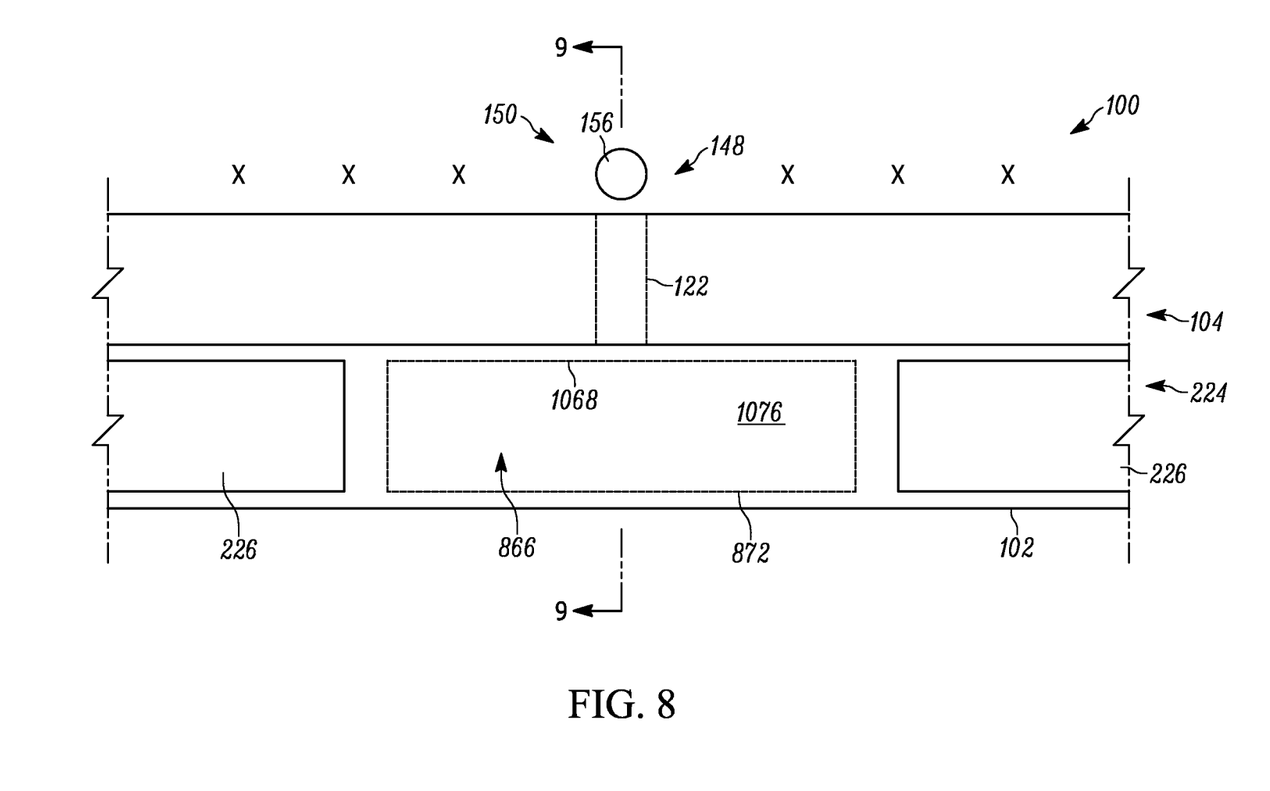
FIG. 8 is a schematic partial front view of the embodiment of FIG. 1.
Figure 9:
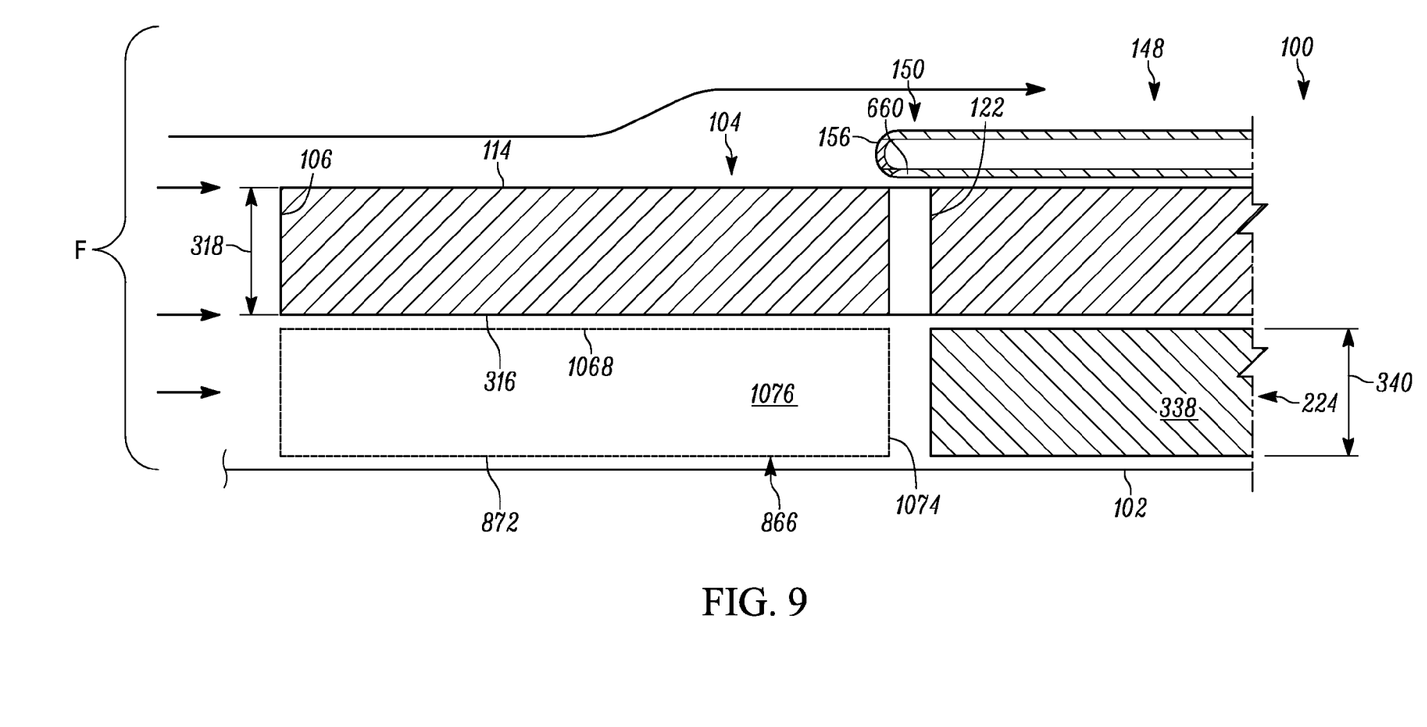
FIG. 9 is a schematic partial cross-sectional view taken along line 9-9 of FIG. 8.
Figure 10:
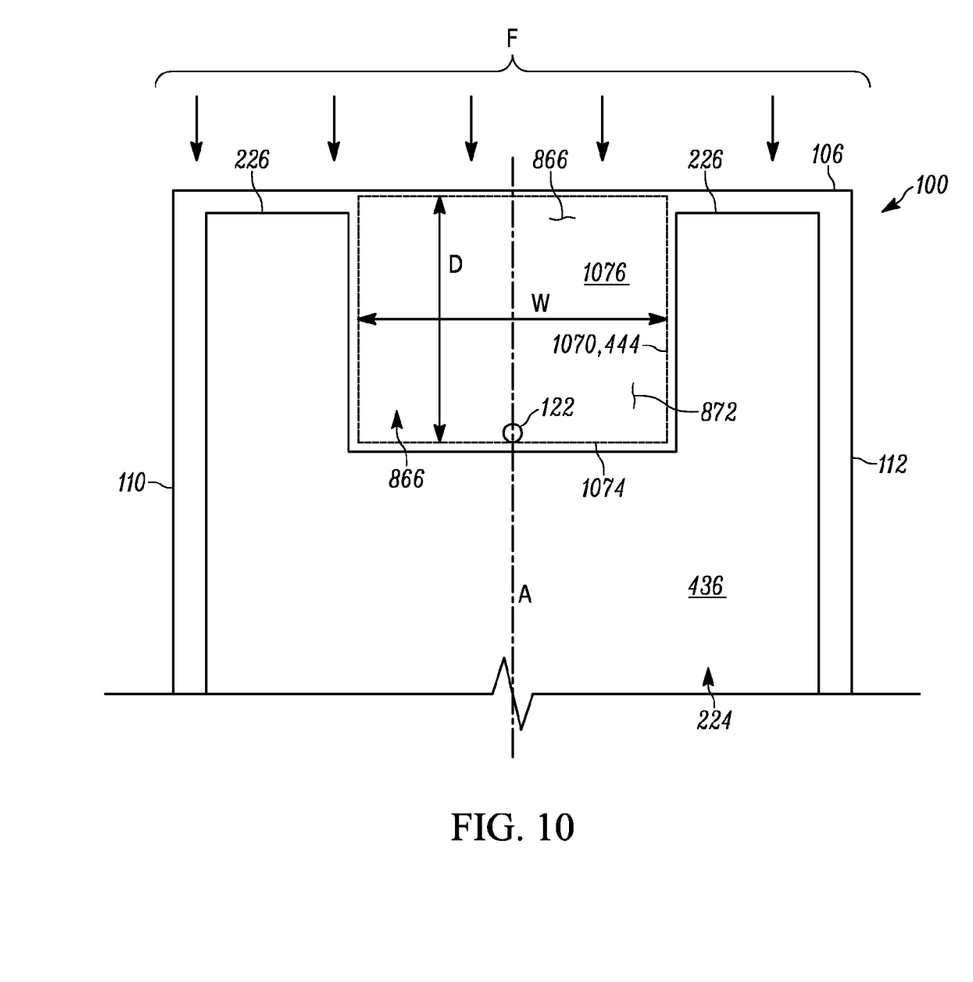
FIG. 10 is a schematic partial bottom view of the embodiment of FIG. 8.

The bounds of the cavity 866 of the apparatus 100 are approximated by the dashed lines in FIGS. 8-10, but the cavity 866 is actually a hollow or indentation having an upper cavity surface 1068 defined by the lower cover surface 316, that upper cavity surface 1068 including the leading cover edge 106 and the cover aperture 122. The cavity 866 has a side cavity perimeter 1070 in the longitudinal-lateral plane which is at least partially defined by the spacer layer perimeter 444. The cavity 866 is in fluid communication with the ambient space at least at the leading spacer edge 226. The cavity 866 may be substantially "sealed" from ingress/egress of fluid other than directly past the leading cover edge 106 and through the cover aperture 122. In the Figures, the spacer layer 224 (made, for example, of transfer tape) includes adhesive features for "sealing", or substantially preventing fluid flow in/near the cavity, in this manner.

Optionally, the cavity 866 may have a substantially constant lateral cavity width W (i.e., the lateral sidewalls of the cavity are substantially parallel), and may have a cavity depth D extending longitudinally from the leading cover edge 106 to a longitudinally spaced cavity trailing wall 1074 defined by at least a portion of the side cavity perimeter 1070. The cover aperture 122 may be substantially adjacent to the cavity trailing wall 1074, but still located in the upper cavity surface 1068 to place the upper cover surface 114 and/or the leading lumen aperture 660 in fluid communication with the cavity 866. In such case, the internal cross-sections of the cavity 866 taken at multiple positions in each of the lateral-transverse and longitudinal-lateral planes will be relatively constant, which may help to simplify fluid dynamics calculations related to the apparatus 100. In other words, the cavity 866 may be substantially symmetrical, in at least the longitudinal-lateral plane, about a longitudinal cavity axis A extending substantially parallel to the measuring tube 148—again, which would likely serve to simplify fluid dynamics calculations related to the apparatus 100.

Stated slightly differently, the cover layer 104, spacer layer 224, and substrate 102 collectively form a cavity 866 having a lateral cavity width W and a longitudinal cavity depth D that are both significantly larger than a transverse cavity height. Optionally, the transverse cavity height can be substantially constant throughout the cavity, which could be an artifact, for example, of the local plane of the cover layer 104 extending substantially parallel to the local plane of the substrate 102.

The cavity 866 is open to the ambient space at a leading edge 106 of the pressure observation device and the cavity 866 is substantially closed, other than through a cover aperture 122 extending through the cover layer 104. The cover aperture 122 may be adjacent a trailing surface 1074 of the cavity 866 longitudinally spaced, in the local variable fluid flow direction, from the leading edge 106 of the pressure observation device 100. Referring briefly back to FIG. 7C, at least a portion of the tube body 154 may extend through the cover layer thickness 318 to place at least a portion of the leading tube end 150 into the cavity 866. This may be done through bending the tube body 154 as shown, "dimpling" up or bending the cover layer 104 to accommodate a substantially straight tube body 154, some combination of these, or in any other suitable manner. However, to avoid local variable fluid flow disturbances that could disrupt the delicate nature of the fluid pressure measurement process, it will be desirable, in many use environments, to avoid substantial protrusion of the leading tube end 150 past the cover layer thickness 318 and into the volume of the cavity 866.

When the lower spacer surface 436 is connected to the substrate 102, as shown in FIGS. 8-9, the substrate 102 defines a lower cavity surface 872. Accordingly, the combination of the substrate 102 and the apparatus 100 collectively enclose five sides of a six-sided "box" cavity which is open to the local longitudinally-oriented variable fluid flow, as shown by flow lines F in FIGS. 9-10. Extant fluid 1076 is at least partially contained within the cavity, and is considered to be substantially stagnant during use of the apparatus 100. Variable fluid flowing in the local fluid flow direction is presented to the apparatus 100, as will be discussed. This variable fluid flow F interacts with the extant fluid 1076, such as by pressing against the extant fluid 1076 at least adjacent to (e.g., at or near) the leading cover edge 106. At least a portion of the variable fluid flowing in the local fluid flow direction exerts pressure upon the extant fluid 1076 to generate an extant fluid pressure level.

Accordingly, during use of the apparatus 100 to measure fluid pressure, variable fluid flowing in the local fluid flow direction pushes against the extant fluid 1076 within the cavity. Optionally, at least a small portion of the variable fluid may enter the cavity 866 at/near the leading cover edge 106. At least a portion of the variable fluid flowing in the local fluid flow direction thus exerts a pressure upon the extant fluid 1076 present in the cavity 866 to generate an extant fluid pressure level. That extant fluid pressure level then propagates through the extant fluid 1076 within the cavity 866 and is physically transmitted from the cavity 866 through the cover aperture 122, via extant fluid 1076 present within/adjacent those structures. The extant fluid pressure level is physically transmitted from the cavity 866 through the cover aperture 122 and into the tube lumen 258 through the leading lumen aperture 660. The extant fluid pressure level is physically transmitted through at least a portion of the tube lumen 258. Depending upon the configuration of the measuring tube 148, the extant fluid pressure level could be physically transmitted through the cover aperture 122 before, during, or after entering the leading lumen aperture 660. All of these physical transmissions of the extant fluid pressure level may be at least substantially facilitated by the presence of extant fluid 1076 within the various structures of the apparatus 100.

More specifically, and as an example of use of this technology, one or more apparatuses 100 could be connected to a substrate 102, such as by being adhered to a surface (e.g., an underside) of an aircraft wing. Because the apparatus 100 does not require a static pressure tap to function as desired, each apparatus 100 can be placed without regard to the locations of any existing static pressure taps. Once the apparatus 100 is in place on the substrate 102 as desired, the cavity 866 will be collectively formed by at least a portion of the lower cover surface 316, the spacer layer perimeter 444, and the substrate 102, with a leading side of the cavity 866 being open to ambient space and a substantially stagnant extant fluid 1076 present within the cavity 866 and the other structures (e.g., the cover aperture 122, measuring tube 148, leading lumen aperture 660, etc.) of the apparatus 100. Once the aircraft is in flight, or variable fluid is otherwise flowing across the substrate 102 in a local fluid flow direction (longitudinally, as shown in the Figures) (the latter situation could occur, for example, if the apparatus 100 is being used within a wind tunnel use environment rather than an in-flight testing use environment), the variable fluid is directed toward the cavity 866, and potentially at least a small portion of the variable fluid will enter the cavity 866. (Conversely, if the variable fluid flow pressure falls below the extant fluid 1076 pressure within the cavity 866, at least a small portion of the extant fluid 1076 could be sucked slightly forward and out of the cavity 866.) Regardless of the location of the variable/extant fluid interface, however, the variable fluid flow interacts with the extant fluid at/near a leading edge of the device, such as adjacent the leading cover edge 106.

The extant fluid pressure level is then physically transmitted (by propagation through the extant fluid therein) through the cover aperture 122 of the cover layer 104 into the leading lumen aperture 660 and thus into the tube lumen 258. At least a portion of extant fluid pressure level transmission into the tube lumen 258 may exist, at least for a brief portion of the transmission path, in a direction substantially transverse to the cover layer 104.

The extant fluid pressure level is then physically transmitted through at least a portion of the tube lumen 258 toward the trailing lumen aperture 162. Finally, at least a portion of the extant fluid pressure level being physically transmitted through the tube lumen 258 will encounter a pressure measuring device 164, such as a pressure transducer, which generates, in any suitable manner, an observer-perceptible extant fluid pressure value in response to the fluid pressure of the extant fluid (i.e., the extant fluid pressure level) within the tube lumen 258. For example, the extant fluid pressure level could be measured to provide the extant fluid pressure value, either at the trailing lumen aperture 162 or spaced therefrom, either inside or outside the measuring tube 148. If the measurement occurs before the extant fluid pressure level reaches the trailing lumen aperture 162, the extant fluid pressure level need not be physically transmitted all the way to the trailing lumen aperture 162. One of ordinary skill in the art will be able to provide a suitable measuring location, type, instrument, and any other corresponding functions/features to generate the extant fluid pressure value for a particular use environment.

The extant fluid pressure value could be based upon, and responsive to, the extant fluid pressure level in any suitable manner, and could be observed by any desired observer and used further in any desired manner. For example, a numerical extant fluid pressure value could be provided to a database and/or made available for further calculations as desired, and in combination with any other desired variables (e.g., local temperature) and/or constants. As another example, a gauge voltage output could be saved in a computer file for later processing and/or displayed on a needle gauge.

The extant fluid pressure values generated using the apparatus 100 may be helpful, for example, in making local skin friction measurements similar to those currently achieved through the use of a Stanton gauge, but without the requirement (of the Stanton gauge) that a static pressure tap be provided. As an example, the skin friction measurements can indicate whether the boundary layer associated with the substrate 102 has airflow in a laminar state, a turbulent state, or a transitional state based on the measurement of the skin friction facilitated by the apparatus 100.

For example, an outputted extant fluid pressure value from the apparatus 100 could be used as an input for a skin friction calculation to provide a skin friction value, in any desired form and using any desired calculation methodology, to an observer and/or to a database for later use. In this example, it may be desirable to use a local static reference pressure value and/or flow temperature as additional inputs for the skin friction calculation. However, that local static reference pressure value can also be obtained without a static pressure tap, through the use of known techniques including, but not limited to, a Sproston & Göksel tube, a strip-a-tube, computational fluid dynamics, pressure-sensitive paint, or any other desired static pressure value-obtaining scheme.

The above description refers to variable fluid as flowing in the local fluid flow direction, such as substantially longitudinal, for the apparatus 100 as shown in the Figures. This approximation is acceptable at least partially due to the relatively small size of the apparatus 100 and the potentially significant variable fluid flow velocities generated, for example, across an aircraft skin surface during flight. However, it should be appreciated that minor local deviations from the prevailing local fluid flow direction are possible, such as slight turbulence within the boundary layer, causing fluctuations of the extant fluid pressure level within the cavity 866, deflection of the variable fluid flow F over or around the apparatus 100 from the substrate 102, or the like.

It is contemplated that one of ordinary skill in the art will readily be able to select appropriate materials and fabrication techniques (or combinations of materials and/or fabrication techniques) for the apparatus 100, or components thereof, based upon factors such as, but not limited to, availability, machinability, ease of use, thermal expansion coefficient and thus applicability in environments (such as flight) with potentially widely varying ambient temperatures, or any other desired factors. For example, it may be desirable to the various components of the apparatus 100 to all be made from materials having similar thermal expansion coefficients for use environments with widely varying ambient temperatures, to prevent damage to the device caused by uneven thermal expansions/contractions.

It is contemplated that the cover layer 104 could have a cover layer thickness 318 which increases in thickness from the leading cover edge 106 to a substantially constant thickness toward the trailing cover edge 108. The cross-sectional shape of this tapering, when present, can be provided in any of a variety of ways, such as, but not limited to, a bevel, cross-sectional diagonal, or a curvilinear cross-section, and the taper could be present at either (i.e., asymmetrically) or both (i.e., symmetrically) of the upper and lower cover surfaces 114 and 316. Thus, the leading cover edge 106 could be "sharp" at the with respect to the airflow, to disturb the airflow entering the cavity 866 to assist with creating a particular type of disturbed pressure within the cavity 866.

It is also contemplated that the pressure change exerted by the variable fluid flow upon the extant fluid within the cavity might be relatively insensitive to a misalignment (e.g., about +/−15 degrees of the nominally longitudinal direction for many use environments) of the cavity "mouth" with the local fluid flow direction. Optionally, the relative directional sensitivity of the apparatus 100 could be used to help provide an indication of the direction of the skin friction at/near the substrate 102. For example, if an apparatus 100 were used at one angle to a reference direction (e.g., 45 degrees), then (the same or another) apparatus 100 were used at another angle to that reference direction (e.g., 0 degrees), the two resulting readings could help facilitate determination of the actual direction and magnitude of skin friction.

For ease of description, the fluids which generally interact with the apparatus 100 are described herein as a variable fluid (flowing in the local fluid flow direction) and a substantially stagnant extant fluid 1076 (present within the cavity 866 and the other structures—e.g., the cover aperture 122, measuring tube 148, leading lumen aperture 660, etc.—of the apparatus 100). The extant fluid pressure values will be physically transmitted "all the way" from the cavity 866 to the measuring device 164 under normal conditions regardless of the exact identity of the fluids within and interacting with the various components of the apparatus 100. However, particularly under steady state conditions, the extant fluid 1076 within the cavity could slightly mix (e.g., due to molecular diffusion) with at least a portion of the variable fluid. This slight mixing, regardless of cause, will not overcome or destroy the "substantially stagnant" nature of the extant fluid 1076 as long as the physical pressure transmission occurs substantially as described above, and one of ordinary skill in the art will understand the fluid interactions involved. A very small amount of "flow" into/out of the cavity will also likely occur during transient fluid flow conditions but will not substantially affect the operation of the apparatus 100 as described.

As a thought experiment related to this molecular diffusion factor, if there is red fluid in the cavity 866 and blue variable fluid flowing past the apparatus 100, then due to a change in speed of the aircraft, some of the blue fluid is pushed into the cavity 866, the originally red extant fluid 1076 in the cavity 866 would slowly turn purple.

For the apparatus 100 as described above, the extant fluid 1076 present within the components will be relatively stagnant (allowing for the small variations as just mentioned and otherwise as understandable by one of ordinary skill in the art) throughout the use of the apparatus 100 to assist with measurement of the variable fluid pressure, as just mentioned. That is, the extant fluid 1076 could shift slightly, such as by becoming compressed under variable fluid pressure, but no significant extant fluid 1076 movement (beyond that which helps to physically transmit the extant fluid pressure level) is contemplated for most use environments. It is also contemplated, however, that a flow path, substantially similar to the physical transmission path described above, could be established for an alternate scheme of pressure measurement. In this alternate scheme, extant fluid will be substantially superseded by a portion of the variable fluid which is permitted to flow through the apparatus 100 from the cavity toward the pressure measuring device 164. Such an alternate, free-flowing embodiment would be facilitated by allowing a substantial portion of the variable fluid flow within the apparatus 100 to ultimately exit the apparatus 100, to avoid unwanted pressurization effects arising within the apparatus 100.

While aspects of this disclosure have been particularly shown and described with reference to the example embodiments above, it will be understood by those of ordinary skill in the art that various additional embodiments may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. The Figures of this application are schematic, and as such, include slight gaps between certain components for ease of understanding; however, one of ordinary skill in the art will be able to understand, with reference to the text of this application, the manner in which the depicted components contact and interrelate. Any of the described structures and components could be integrally formed as a single unitary or monolithic piece or made up of separate sub-components, with either of these formations involving any suitable stock or bespoke components and/or any suitable material or combinations of materials. Any of the described structures and components could be disposable or reusable as desired for a particular use environment. Any component could be provided with a user-perceptible marking to indicate a material, configuration, at least one dimension, or the like pertaining to that component, the user-perceptible marking aiding a user in selecting one component from an array of similar components for a particular use environment. A "predetermined" status may be determined at any time before the structures being manipulated actually reach that status, the "predetermination" being made as late as immediately before the structure achieves the predetermined status. Though certain components described herein are shown as having specific geometric shapes, all structures of this disclosure may have any suitable shapes, sizes, configurations, relative relationships, cross-sectional areas, or any other physical characteristics as desirable for a particular application. Regardless of the exact configuration of the leading lumen aperture 660 and cover aperture 122, it will be desirable for many use environments to substantially prevent interposition of variable fluid into the extant fluid path between these structures. It will be desirable, for most use applications of the apparatus 100, that the leading spacer edge 226, substrate 102, and cover layer 104 to collectively form a "mouth", or front cavity face, that is substantially rectangular. For most use environments, the cover aperture 122 will be located significantly longitudinally spaced from the leading cover edge 106, though one of ordinary skill in the art can provide a physical arrangement of these components and/or any other structures of the apparatus 100 as desired. Some form of caulking (not shown) or other sealing-assistance material may be provided to assist with substantially preventing undesirable fluid flow through/into/from the cavity 866. At least a portion of the lower cover layer surface 316 could be machined or otherwise physically altered (e.g., in a "U" shape similar to that of the spacer layer 224) to contribute to a height of the cavity 866 as extending transversely upward from the spacer layer 224 and into the cover layer thickness 318. The cavity 866, or any other portion of the apparatus 100, could include internal baffles, ducting, or other structures for altering fluid flow from that shown and described herein, or for any other desired purpose. Any structures or features described with reference to one embodiment or configuration could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

We claim:

1. An apparatus for assisting with measurement of the pressure of a variable fluid flowing past a substantially planar, constant-surface substrate in a substantially linear and longitudinal local fluid flow direction, the apparatus comprising:

a substantially planar cover layer having longitudinally spaced leading and trailing cover edges, laterally spaced first and second cover side edges, and oppositely facing upper and lower cover surfaces transversely separated by a cover layer thickness, at least the lower cover surface defining a cover layer footprint in a longitudinal-lateral plane, and a cover aperture extending through the cover layer thickness to fluidly connect the upper and lower cover surfaces;

a substantially planar spacer layer having longitudinally spaced leading and trailing spacer edges, laterally spaced first and second spacer side edges, and oppositely facing upper and lower spacer surfaces transversely separated by a spacer layer thickness, at least the lower spacer surface defining a spacer layer footprint in the longitudinal-lateral plane, the spacer layer footprint having a smaller area than the area of the cover layer footprint, and the spacer layer footprint being bounded in the longitudinal-lateral plane by a spacer layer perimeter;

a cavity having an upper cavity surface defined by the lower cover surface, the upper cavity surface including the leading cover edge and the cover aperture, and the cavity having a side cavity perimeter in the longitudinal-lateral plane at least partially defined by the spacer layer perimeter; and a measuring tube having leading and trailing tube ends longitudinally separated by a tube body, the measuring tube being located adjacent to the upper cover surface, the leading tube end having a length which is a superminority of the length of the tube body, the measuring tube including a tube lumen extending longitudinally through the tube body between a leading lumen aperture at the leading tube end and a trailing lumen aperture longitudinally spaced from the leading lumen aperture, the leading lumen aperture being in fluid communication with the cavity via the cover aperture, and the trailing lumen aperture being in fluid communication with a pressure measuring device;

wherein, when the lower spacer surface is connected to the substrate, the substrate defines a lower cavity surface, extant fluid being at least partially contained within the cavity, and variable fluid flowing in the substantially linear and longitudinal local fluid flow direction interacts with the extant fluid within the cavity at least adjacent the leading cover edge, and at least a portion of the variable fluid flowing in the substantially linear and longitudinal local fluid flow direction exerting pressure upon the extant fluid to generate an extant fluid pressure level which is physically transmitted from the cavity through the cover aperture, into the tube lumen through the leading lumen aperture, and is made available for measurement, as an extant fluid pressure value, through at least a portion of the tube lumen.

2. The apparatus of claim 1, wherein the leading lumen aperture is at a longitudinally forward tip of the leading tube end.

3. The apparatus of claim 1, wherein the leading lumen aperture is located at the leading tube end and is longitudinally spaced back from a longitudinally forward tip of the leading tube end.

4. The apparatus of claim 1, wherein a pressure measuring device measures the extant fluid pressure level, to generate the extent fluid pressure value, by fluid communication with the extant fluid through the trailing lumen aperture.

5. The apparatus of claim 1, wherein at least a portion of the lower spacer surface includes an adhesive configured to selectively adhere the apparatus to the substrate.

6. The apparatus of claim 1, wherein at least a portion of the leading tube end extends through at least a portion of the cover aperture.

7. The apparatus of claim 6, wherein at least a portion of the tube body extends through the cover layer thickness to place at least a portion of the leading tube end into the cavity.

8. The apparatus of claim 1, wherein the cavity has a substantially constant lateral cavity width and has a cavity depth extending from the leading cover edge to a longitudinally spaced cavity trailing wall defined by at least a portion of the side cavity perimeter, the cover aperture being adjacent to the cavity trailing wall.

9. An apparatus for assisting with measurement of a boundary layer pressure of a variable fluid flowing through an ambient space past a substantially planar, constant-surface substrate in a substantially linear and longitudinal local fluid flow direction, the apparatus comprising:

a substantially planar cover layer having longitudinally spaced leading and trailing cover edges, laterally spaced first and second cover side edges, and oppositely facing upper and lower cover surfaces transversely separated by a cover layer thickness, and a cover aperture extending through the cover layer thickness to fluidly connect the upper and lower cover surfaces;

a substantially planar spacer layer having longitudinally spaced leading and trailing spacer edges, laterally spaced first and second spacer side edges, and oppositely facing upper and lower spacer surfaces transversely separated by a spacer body having a spacer layer thickness, the spacer layer defining a spacer layer perimeter in a longitudinal-lateral plane, the spacer layer perimeter defining a concave extension into the spacer body which bifurcates the leading spacer edge but is longitudinally spaced from the trailing spacer edge;

a cavity having an upper cavity surface defined by the lower cover surface, the upper cavity surface including a cover aperture, and the cavity having a side cavity perimeter in the longitudinal-lateral plane at least partially defined by concave extension of the spacer layer perimeter, the cavity being in fluid communication with the ambient space at the leading spacer edge; and a measuring tube having leading and trailing tube ends longitudinally separated by a tube body, the measuring tube being located adjacent to the upper cover surface, the leading tube end having a length which is a superminority of the length of the tube body, the measuring tube including a tube lumen extending longitudinally through the tube body between a leading lumen aperture at the leading tube end and a trailing lumen aperture longitudinally spaced from the leading lumen aperture, the leading lumen aperture being in fluid communication with the cavity via the cover aperture, and the trailing lumen aperture being in fluid communication with a pressure measuring device;

wherein, when the lower spacer surface is connected to the substrate, the substrate defines a lower cavity surface, extant fluid being at least partially contained within the cavity, and variable fluid flowing in the substantially linear and longitudinal local fluid flow direction interacts with the extant fluid within the cavity at least adjacent the leading cover edge, and at least a portion of the variable fluid flowing in the substantially linear and longitudinal local fluid flow direction exerting pressure upon the extant fluid to generate an extant fluid pressure level which is physically transmitted from the cavity through the cover aperture, into the tube lumen through the leading lumen aperture, and is made available for measurement, as an extant fluid pressure value, through at least a portion of the tube lumen.

10. The apparatus of claim 9, wherein the leading lumen aperture is at a longitudinally forward tip of the leading tube end.

11. The apparatus of claim 9, wherein the leading lumen aperture is located at the leading tube end and is longitudinally spaced back from a longitudinally forward tip of the leading tube end.

12. The apparatus of claim 9, wherein a pressure measuring device measures the extant fluid pressure level, to generate the extant fluid pressure value, by fluid communication with the extant fluid through the trailing lumen aperture.

13. The apparatus of claim 9, wherein at least a portion of the lower spacer surface includes an adhesive configured to selectively adhere the apparatus to the substrate.

14. The apparatus of claim 9, wherein at least a portion of the leading tube end extends through at least a portion of the cover aperture.

15. The apparatus of claim 14, wherein at least a portion of the tube body extends through the cover layer thickness to place at least a portion of the leading tube end into the cavity.

16. The apparatus of claim 9, wherein the cavity is substantially symmetrical, in the longitudinal-lateral plane, about a longitudinal cavity axis extending substantially parallel to the measuring tube.

17. A method of assisting with measurement of the pressure of a variable fluid flowing through an ambient space past a substantially planar, constant-surface substrate in a substantially linear and longitudinal local fluid flow direction, the method comprising:

providing a pressure observation device for assisting with measurement of the pressure of a variable fluid flowing past a substantially planar, constant-surface substrate in a substantially linear and longitudinal local fluid flow direction, the pressure observation device including a substantially planar cover layer having longitudinally spaced leading and trailing cover edges, laterally spaced first and second cover side edges, and oppositely facing upper and lower cover surfaces transversely separated by a cover layer thickness, at least the lower cover surface defining a cover layer footprint in a longitudinal-lateral plane, and a cover aperture extending through the cover layer thickness to fluidly connect the upper and lower cover surfaces, a substantially planar spacer layer having longitudinally spaced leading and trailing spacer edges, laterally spaced first and second spacer side edges, and oppositely facing upper and lower spacer surfaces transversely separated by a spacer layer thickness, at least the lower spacer surface defining a spacer layer footprint in the longitudinal-lateral plane, the spacer layer footprint having a smaller area than the area of the cover layer footprint, and the spacer layer footprint being bounded in the longitudinal-lateral plane by a spacer layer perimeter, a cavity having an upper cavity surface defined by the lower cover surface, the upper cavity surface including the leading cover edge and the cover aperture, and the cavity having a side cavity perimeter in the longitudinal-lateral plane at least partially defined by the spacer layer perimeter, and a measuring tube having leading and trailing tube ends longitudinally separated by a tube body, the measuring tube being located adjacent to the upper cover surface, the leading tube end having a length which is a superminority of the length of the tube body, the measuring tube including a tube lumen extending longitudinally through the tube body between a leading lumen aperture at the leading tube end and a trailing lumen aperture longitudinally spaced from the leading lumen aperture, the leading lumen aperture being in fluid communication with the cavity via the cover aperture, and the trailing lumen aperture being in fluid communication with a pressure measuring device;

adhering the lower spacer surface of the pressure observation device to the substrate such that the substrate defines a lower cavity surface and extant fluid is at least partially contained within the cavity;

directing variable fluid flow in the substantially linear and longitudinal local fluid flow direction toward the cavity pressure observation device to interact with the extant fluid within the cavity at least adjacent the leading cover edge of the pressure observation device;

with at least a portion of the variable fluid flowing in the substantially linear and longitudinal local flow direction, exerting pressure upon the extant fluid within the cavity to generate an extant fluid pressure level;

physically transmitting the extant fluid pressure level from the trailing surface of the cavity through the cover layer via the cover aperture;

physically transmitting the extant fluid pressure level through the cover aperture of the cover layer into the leading lumen aperture;

physically transmitting the extant fluid pressure level through at least a portion of the tube lumen toward the trailing lumen aperture; and generating an extant fluid pressure value in response to the extant fluid pressure level at the trailing lumen aperture.

18. The method of claim 17, wherein physically transmitting the extant fluid pressure level from the trailing surface of the cavity through the cover layer via the cover aperture includes physically transmitting the extant fluid pressure level in a direction substantially transverse to the cover layer.

19. The method of claim 17, wherein providing the pressure observation device with a measuring tube includes providing the pressure observation device with a measuring tube having the leading lumen aperture at a longitudinally forward tip of the leading tube end.

20. The method of claim 17, wherein providing the pressure observation device with a measuring tube includes providing the pressure observation device with a measuring tube having the leading lumen aperture located at the leading tube end and longitudinally spaced back from a longitudinally forward tip of the leading tube end.

* * * * *